United States Patent
Kadlec et al.

(10) Patent No.: US 6,869,518 B2
(45) Date of Patent: Mar. 22, 2005

(54) ELECTROCHEMICAL GENERATION OF CHLORINE DIOXIDE

(75) Inventors: Leonard J. Kadlec, Woodbury, MN (US); Patrick H. Kilawee, Hugo, MN (US)

(73) Assignee: Ecolab Inc., Mendota Heights, MN (US)

(*) Notice: Subject to any disclaimer, the term of this patent is extended or adjusted under 35 U.S.C. 154(b) by 65 days.

(21) Appl. No.: 10/171,223

(22) Filed: Jun. 12, 2002

(65) Prior Publication Data

US 2003/0230492 A1 Dec. 18, 2003

(51) Int. Cl.⁷ .............................. C25B 1/26; F25C 1/00
(52) U.S. Cl. ................... 205/556; 205/500; 204/229.4; 204/258; 62/69; 62/78
(58) Field of Search ................ 205/556, 500; 62/69, 78; 204/229.4, 258

(56) References Cited

U.S. PATENT DOCUMENTS

| | | | |
|---|---|---|---|
| 2,163,793 A | 6/1939 | Logan | 204/9 |
| 4,017,373 A | 4/1977 | Shaw et al. | 204/195 |
| 4,542,008 A | 9/1985 | Capuano et al. | 423/477 |
| 4,853,096 A | 8/1989 | Lipsztajn et al. | 204/101 |
| 5,092,970 A | 3/1992 | Kaczur et al. | 204/98 |
| 5,106,465 A | 4/1992 | Kaczur et al. | 204/98 |
| 5,158,658 A | 10/1992 | Cawlfield et al. | 204/252 |
| 5,289,691 A | 3/1994 | Schlosser et al. | 62/78 |
| 5,367,283 A | 11/1994 | Lauf et al. | 338/34 |
| 5,408,834 A | 4/1995 | Schlosser et al. | 62/78 |
| 5,586,439 A | 12/1996 | Schlosser et al. | 62/78 |
| 5,787,723 A | 8/1998 | Mueller et al. | 62/347 |
| 5,878,583 A | 3/1999 | Schlosser et al. | 62/73 |
| 5,974,810 A * | 11/1999 | Speronello | 62/66 |
| 6,203,688 B1 * | 11/1999 | Speronello | 205/556 |
| 6,196,007 B1 | 3/2001 | Schlosser et al. | 62/73 |
| 6,274,009 B1 | 8/2001 | Krafton et al. | 204/230.2 |
| 6,306,281 B1 | 10/2001 | Kelley | 205/556 |
| 6,324,863 B1 * | 12/2001 | Henry | 62/347 |

* cited by examiner

Primary Examiner—Arun S. Phasge
(74) Attorney, Agent, or Firm—Vidas, Arrett & Steinkraus

(57) ABSTRACT

A method of producing chlorine dioxide gas in an enclosed space including the steps of electrochemically generating chlorine dioxide gas in an electrochemical cell and transporting the chlorine dioxide gas to the enclosed space.

26 Claims, 5 Drawing Sheets

US 6,869,518 B2

ELECTROCHEMICAL GENERATION OF CHLORINE DIOXIDE

FIELD OF THE INVENTION

The present invention relates to a device and method for extending the time between cleaning while deodorizing a unit having an enclosed space not otherwise easily accessible for cleaning and deodorizing. The device and method of the present invention utilize the generation of an antimicrobial gas in an amount effective to reduce microbial populations including germs and fungi.

BACKGROUND OF THE INVENTION

Chlorine dioxide has been found to be an especially effective disinfectant. As used herein, the term "disinfecting" shall be used to include sanitizing, deodorizing, sterilizing, or otherwise destroying or reducing germ populations. The term "germs" as used herein shall include bacteria, yeasts, molds, viruses or any micro-organism whose presence, and numbers, are deemed inimical to human or animal welfare. Its use has been found to be particularly advantageous where microbes and/or organic odorants are sought to be controlled on and around foodstuffs, as chlorine dioxide functions without the formation of undesirable side products such as chloramines or chlorinated organic compounds that can be produced when elemental chlorine is utilized for the same or similar purposes.

Additionally, at concentrations which have been found to be effective for deodorization and for most antimicrobial applications, chlorine dioxide gas is also generally considered as safe for human contact because the concentrations required are so low.

Certain difficulties are encountered with the use of chlorine dioxide in practice, however. Chlorine dioxide gas can be toxic to humans at concentrations greater than 1,000 ppm and it can be explosive at partial pressures above about 0.1 atmosphere. Therefore, chlorine dioxide gas is not manufactured and shipped under pressure like other industrial gases, and conventional methods of on-site manufacture require not only expensive generation equipment but also high levels of operator skill to avoid generating dangerously high concentrations. These problems have substantially limited the use of chlorine dioxide to large commercial applications, such as water treatment and poultry processing, where the consumption of chlorine dioxide is sufficiently large that it can justify the capital and operating costs of expensive equipment and skilled operators for on-site manufacture. However, it is not practical to ship chlorine dioxide as a concentrated gas to the medium or small users.

It has thus become common practice to employ a chlorine dioxide-liberating compound such as sodium chlorite powder which is much safer from the standpoints of storage, shipping and handling. Generation of the chlorine dioxide from sodium chlorite or other chlorine dioxide liberating compound is usually effected by addition of acid, bleach (hypochlorite), or chlorine to the chlorine dioxide liberating compound.

However, the composition obtained from the interaction of the relatively high concentrations of sodium chlorite and acid materials used can be injurious to health. Significantly, the toxicity problem imposes severe limitations on the general utility of the disinfectant composition, particularly with respect to the treatment of human beings.

Methods have been developed in an attempt to overcome the aforementioned problems, but improved methods of generating chlorine dioxide on a small scale are still desired.

SUMMARY OF THE INVENTION

The present invention relates to a method and device for producing chlorine dioxide gas in an enclosed space including electrochemically generating chlorine dioxide gas in an electrochemical cell and transporting the chlorine dioxide gas to the enclosed space.

The present invention relates to the electrochemical generation of chlorine dioxide for use in deodorizing and sanitizing of enclosed spaces. The device and method of the present invention allow for the controlled and sustained release of chlorine dioxide gas. The chlorine dioxide may be generated inside the enclosure by installing the electrochemical device inside the enclosure, or the chlorine dioxide may be transported into the enclosure such as through a tube or by venting.

More specifically, the present invention relates to a method of generating an antimicrobially active gas including the steps of providing an aqueous metal chlorite composition which reacts in an electrolytic cell to produce chlorine dioxide gas for deodorizing and sanitizing in an enclosed environment.

More particularly, the unit of the present invention with which the unit of the present invention has an interior and an exterior. The electrolytic cell is placed in the interior of the unit. The unit further may have an access port to allow easy replacement of the aqueous chlorine dioxide producing composition from the exterior of the unit, or to replace the electrolytic cell if it is disposable.

In some embodiments of the present invention, the unit has a top and a front and the holder is in the front or top of the unit. The unit may also have sides and/or a back or bottom in which the holder may be placed. Suitably, the holder is in a convenient location which is easily accessible.

The release of the gas can be controlled and sustained using the method, composition and device of the present invention.

The device and method find particular utility for treating automatic ice making machines.

The present invention is particularly useful for deodorizing/sanitizing in relatively small enclosed spaces such as storage lockers which are smaller than about 800 cubic feet, and in ice machines which have enclosures of less than about 3 cubic feet.

The device of the present invention allows generation of chlorine dioxide with aqueous compositions of metal chlorite using less than 1000 ml of the composition, and more suitably, about 25 mls to about 100 mls.

DETAILED DESCRIPTION OF THE PREFERRED EMBODIMENTS

While this invention may be embodied in many different forms, there are described in detail herein specific embodiments of the invention. This description is an exemplification of the principles of the invention and is not intended to limit the invention to the particular embodiments illustrated.

The present invention is directed to a method, composition and device for the controlled and sustained release of a deodorizing and/or antimicrobially active gas over a period of time. The reactants and device of the present invention are designed such that low levels of the antimicrobially active gas may be released over an extended period of time for deodorization and sanitization. The rate and duration of the release of gas may be controlled using the composition and device of the present invention. This rate of release may be controlled by controlling the amount of power being supplied to the electrodes of the electrolytic cell.

The process employed in the present invention involves the electrolytic production of chlorine dioxide in both solution and in a gaseous state using an aqueous solution of a metal chlorite. The electrolytic cell has both an anode and a cathode which may or may not be separated by a separator such as a membrane.

Figure 1:
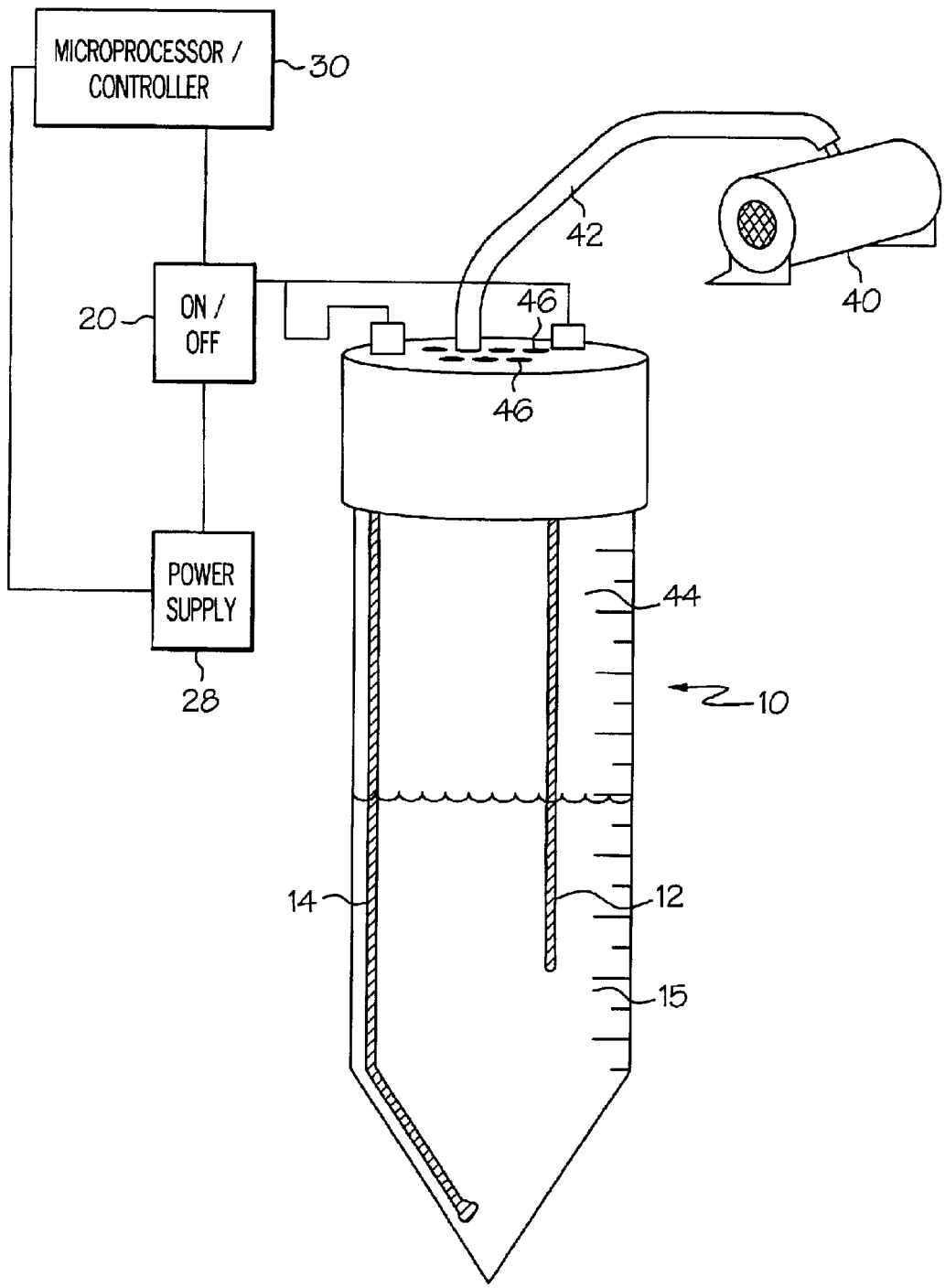
FIG. 1 illustrates one embodiment of the electrolytic cell according to the present invention.

Turning now to the figures, FIG. 1 illustrates one embodiment of the present invention in which an electrolytic cell shown generally at 10 contains an aqueous metal chlorite composition 15 at a concentration of about 25%. In this embodiment, no separator is employed. Cell 10 has a cathode 12 and an anode 14 each of which is constructed of copper. If no separator is employed as described in detail below, cathode 12, may be isolated from anode 14 using any means known in the art to prevent disrupting the flow of current. For example, a polymeric sleeve may be employed over the cathode for such a purpose.

A relay switch 20 in communication with the cathode 12 and the anode 14 may be set to cycle on and off for controlling the amount of time the chlorine dioxide is generated. The power source 28 for the device may be either direct current (DC) or alternating current (AC). A microprocessor/controller may be optionally employed.

Chlorine dioxide gas is produced from sodium chlorite in the electrochemical process as described above according to the following half-cell reactions:

| Anode: | $2Na^+ + 2ClO_2^- \rightarrow 2Na^+ + 2ClO_2 + 2e^-$ |
| Cathode: | $2H_2O + 2e^- \rightarrow 2OH^- + H_2$ |

Chlorine dioxide is thus formed at the anode while sodium hydroxide is formed at the cathode.

The device of FIG. 1 is shown equipped with an air pump 40 which is in communication with said electrochemical cell 10 through the use of a conduit 42. Conduit 42 may be formed of any suitable material known in the art. Air pump 40 supplies air to said head space 44 above the aqueous composition 15 purging the head space 44 of the electrolytic cell 10 of chlorine dioxide gas which then is forced out through the vent holes 46 in the top of the electrolytic cell. Alternatively, rather than being equipped with vent holes 46, the device may be equipped with a conduit as shown at 22 in FIG. 4 or at 26 in FIG. 5 which can transport the chlorine dioxide gas from outside of the headspace.

The hydrogen produced as a by-product of the reaction may be removed from the vessel, or allowed to escape into the atmosphere. Alternatively, hydrogen gas may be collected and compressed for storage and later may be used for power generation, or to supply a fuel cell for immediate use. A hydrogen sensor may also be optionally installed in the device. Such a sensor is described in U.S. Pat. No. 5,367,283 incorporated by reference herein in its entirety.

Figure 2:
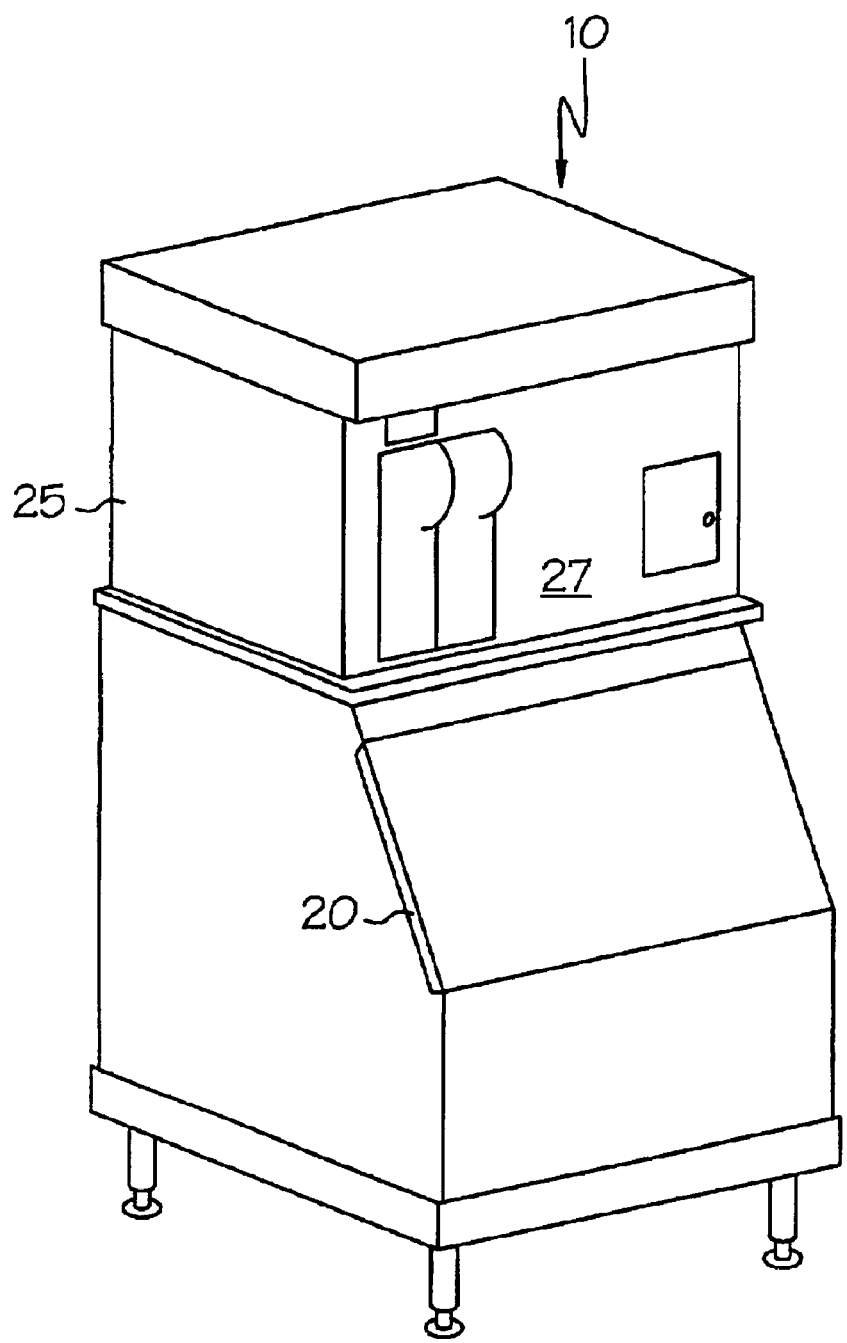
FIG. 2 shows an automatic ice making unit.
Figure 3:
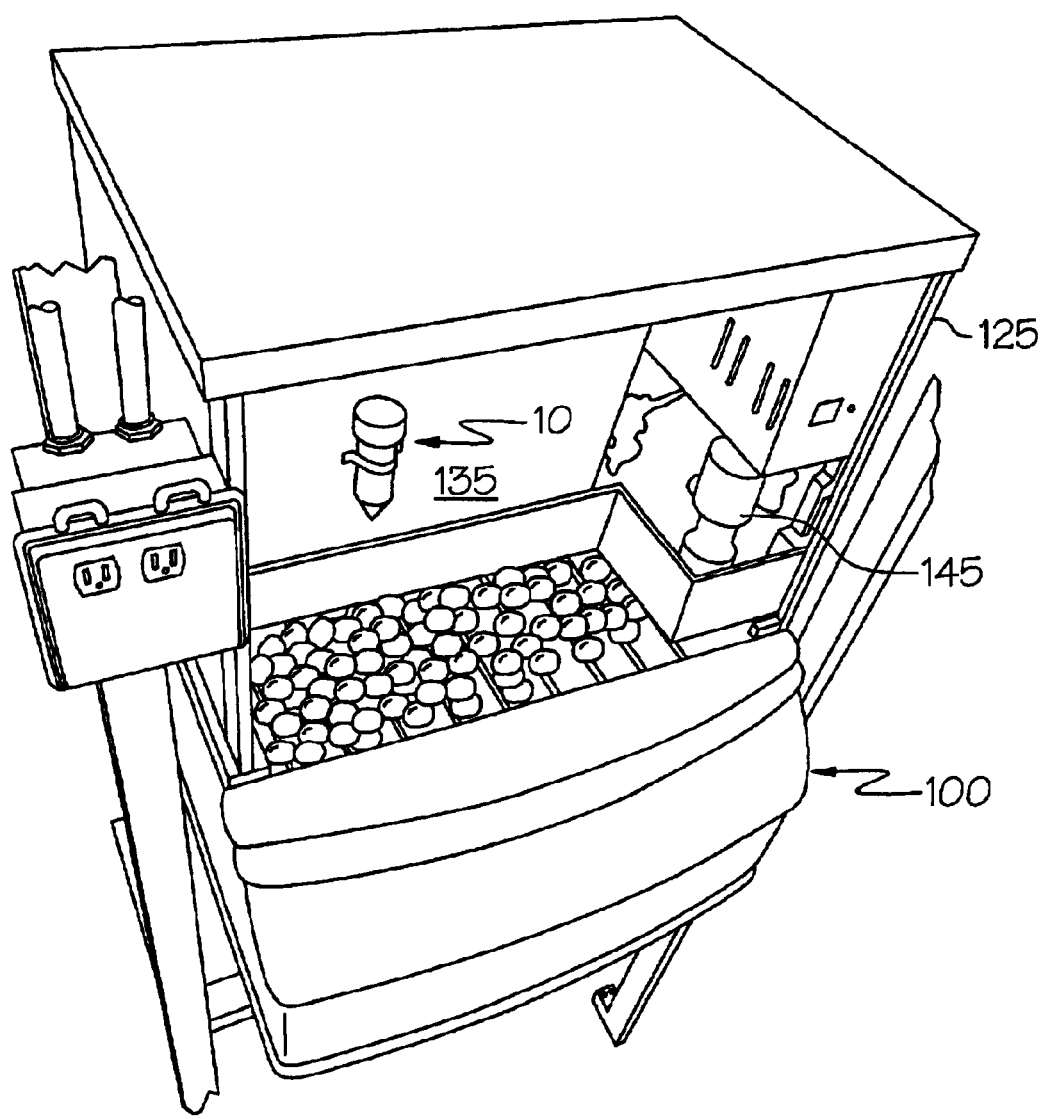
FIG. 3 shows the head space of an automatic ice making unit with an electrolytic cell as described in FIG. 1.
Figure 4:
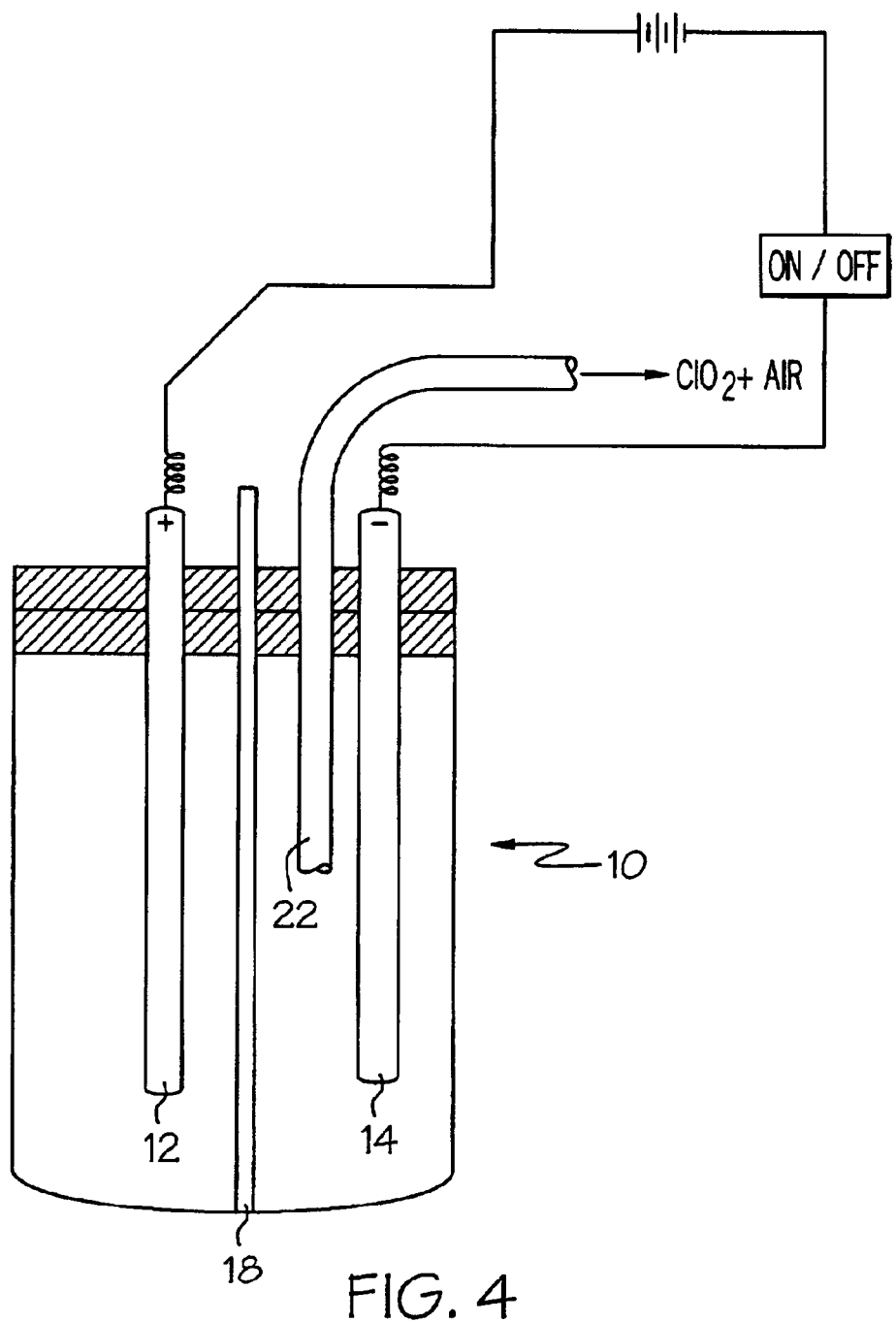
FIG. 4 shows an alternative embodiment of an electrolytic cell according to the present invention.

In one embodiment of the present invention, the device described above is employed in combination with an automatic ice making machine shown generally at 100, of a type similar to that shown in FIG. 2, for example. In this example, an electrolytic cell 10, of the type described above, is installed in the head space 135 of the ice making machine 100. Alternatively, the device may be installed outside of the headspace, and the chlorine dioxide gas transported through a tube and into the headspace as shown in FIGS. 4 at 22 or FIG. 5 at 26, for example.

The electrolytic cell may be further equipped with a recycling relay as shown in FIG. 1 which may be optionally "plugged in" to the circuitry of the automatic ice making machine 100 which already has a microprocess/controller shown at 30 in FIG. 1, and programmed to run at certain time intervals cycling between off and on.

Automatic ice making machines are described in U.S. Pat. Nos. 5,289,691, 5,408,834, 5,586,439, 5,787,723, 5,878,583, 6,196,007 B, and so forth, each of which is incorporated by reference herein in its entirety. These ice machines are intended for exemplary purposes only. One of skill in the art would understand that various modifications could be made to the ice machines described herein, and that other completely different configurations could be utilized without departing from the scope of the present invention.

Other types of electrolytic cells may be employed in the present invention as well. FIG. 4 shows generally at 50 a simplified version of an alternative embodiment of an electrolytic cell wherein a solution of a chlorite and a chloride of an alkali or alkaline earth metal is electrolyzed and chlorine dioxide is produced at the anode 14 and hydrogen gas is liberated at the cathode 12 according to the following general reaction:

$$2NaCl + 2NaClO_2 + H_2O \rightarrow 2ClO_2 + 2NaCl + 2NaOH + H_2$$

The electrodes may be formed of any suitable conducting material including, but not limited to, graphite, copper, stainless steel, nickel, and so forth.

The anode compartment and the cathode compartment are separated by a porous membrane 18 which is sufficiently porous to permit a satisfactory flow of solution without allowing any substantial amount of diffusion from one compartment to another. One of ordinary skill in the art knows of such porous membranes.

A flow tube 22 is provided for removal of the chlorine dioxide produced at the anode 14. The flow tube may be optionally connected to an air pump.

The electrolytic cell 10 is also provided with a relay switch for cycling the cell to on/off modes in order to control how much chlorine dioxide is being produced. The level of chlorine dioxide produced should be enough to reduce microbial populations, i.e. between about 0.01 ppm and about 20 ppm, and more suitably about 0.05 ppm to about 15 ppm, but should not be so high as to be toxic to humans. Electrolytic cells of a similar type are described in U.S. Pat. No. 2,163,793 the content of which is incorporated by reference herein in its entirety.

Figure 5:
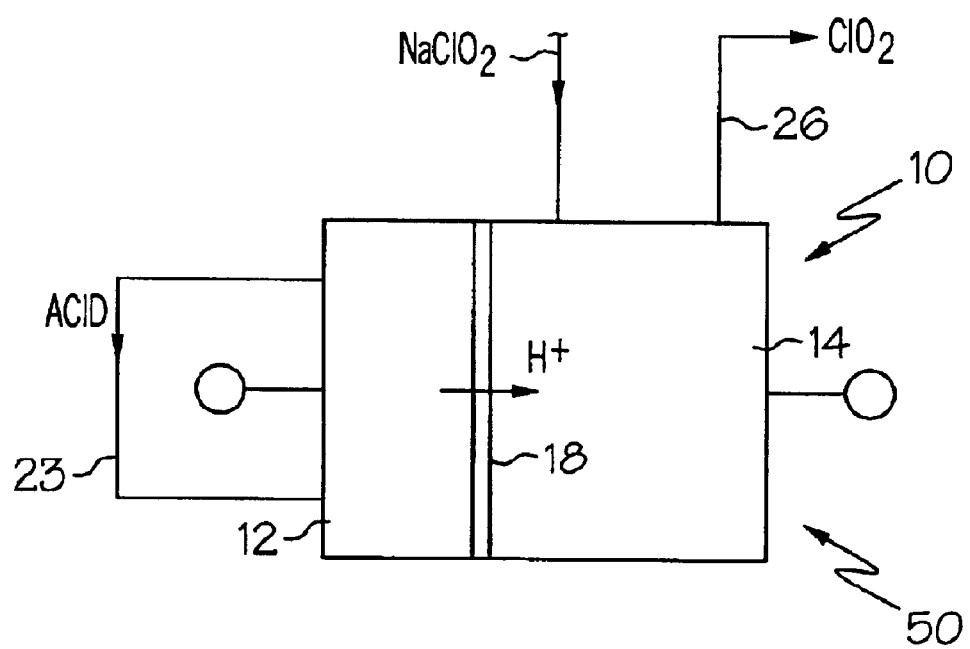
FIG. 5 shows an alternative embodiment of an electrolytic cell according to the present invention.

FIG. 5 shows generally at 10 a simplified version of an alternative type of electrolytic cell useful in the present invention. Numerous variations may be made on the type of cell shown in FIG. 5, but in general, the cell will include a cathode compartment 12, an anode compartment 14, and a separator 18 separating the cathode compartment 12 from the anode compartment 14.

In this type of cell, a solution of an anolyte such as a non-oxidizable acid, including, for example, sulfuric, phosphoric, nitric and so forth is fed to the anode compartment 12, and an aqueous solution of an alali metal chlorite is provided in the cathode compartment 14, the anolyte and catholyte being separated by any suitable separator such as an ion exchange membrane 18. The anolyte in the anode compartment is electrolyzed to generate hydrogen ions. The hydrogen ions are passed from the anode compartment through the membrane into the ion exchange compartment to displace alkali metal ions and produce an aqueous solution of chlorine dioxide. The alkali metal ions from the ion exchange compartment are passed into the cathode compartment. An example of this type of cell is described in U.S. Pat. No. 5,092,970 and U.S. Pat. No. 5,106,465.

Chlorine dioxide gas is also produced in the cathode compartment 14 and is vented from the electrolytic cell 50 by line 26. Alternatively, vent holes (not shown) may be provided in the top of the cathode compartment 14 similar to those shown in FIG. 1.

Other additives including, for example, buffers, may be employed to control the pH and/or to promote more efficient conversion of chlorite to chlorine dioxide and to suppress chlorite ion formation. Such additives include, but are not limited to, inorganic alkali metal salts such as chlorides, phosphates, sulfates, nitrates, nitrites, carbonates, borates, and the like as well as organic alkali metal salts including, but not limited to, tartrates, citrates, acetates, formates, oxalates, gluconates, phthalates, benzoates, salicylates, and so forth. Particularly useful alkali metals include potassium, sodium and lithium.

In an embodiment wherein an alkali metal chloride is added, the reaction may be illustrated by the following general chemical equation:

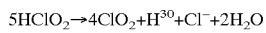

$$5HClO_2 \rightarrow 4ClO_2 + H^{3O} + Cl^- + 2H_2O$$

The electrolytic cell described above is one method of producing chlorine dioxide, but other types of electrolytic cells employing other half-cell reactions may also be employed.

It is possible to operate the cell and the instant process with any appropriate separator, not merely a cation exchange membrane, as long as the separator is permeable to anions and cations to obtain the required electrical conductivity therethrough. Any microporous separator is acceptable and where an aqueous acid composition is used as the catholyte, the separator can be a diaphragm of the type used in diaphragm electrolytic cells. In this case some back migration of anions from the catholyte compartment to the anolyte compartment is expected and may be permissible, depending upon the application of the final product.

The aqueous acid composition may include any appropriate acid including, but not limited to, hydrochloric, sulfuric, phosphoric, nitric, acetic, lactic, and so forth.

Other appropriate electrolytic cells employing a separator, may be found in U.S. Pat. Nos. 6,274,009, and 6,203,688 each of which are incorporated by reference herein in their entirety.

There are a numerous types of electrolytic cells which may be employed in the present invention to produce a limited and controlled quantity of chlorine dioxide. Such electrolytic cells are known to those of ordinary skill in the art.

The power supply 28, shown in FIG. 1, may be either direct current (DC) or alternating current (AC). In the case of a DC power source, the power source may be anywhere from about 3 volts up to about 20 volts, and is advantageously in the range of about 6 to about 18 volts. In one embodiment, four D cell batteries are employed at about 6 volts. The electrical potential of the $ClO_2$ electrochemical reaction is +0.954 volts. This is thus the minimum amount of voltage needed to create $ClO_2$ from an aqueous solution. The higher the voltage, the more $ClO_2$ released.") A low battery indicator such as an LED or alarm may also be optionally included with the device.

The device as described in the present invention is advantageously employed on a small scale. For example, aqueous compositions of the chlorite may be employed in amounts of 1000 ml or less, and suitably, in amounts of 25 ml to 100 ml.

The present invention may be utilized in any application where it is desirable to deodorize, or where it is desirable to reduce the population of microbes present including fungi, molds, yeast, slimes, bacteria, and so forth, other microbiological growths, and so forth. Using the present invention, the amount of chlorine dioxide generated may vary from anywhere between about 0.01 to about 20 ppm, and more suitably about 0.05 ppm to about 15 ppm, with deodorizing typically occurring at the lower end of the concentration range of as little as 1 ppm or less.

The present invention is advantageously employed in small enclosures of 800 cubic feet or less. In some applications, the enclosure is less than 3 cubic feet. In addition to its utility in ice making machines, the device and method of the present invention may be employed in other refrigeration units including soda machines, produce storage lockers, garbage receptacles, cleaning equipment/supply lockers, gym lockers, closets, bathroom stalls, wet bars, and so forth.

The small size of the device of the present invention, allows the device to be portable which is another advantage.

The embodiments described herein will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

The following non-limiting examples further illustrate the present invention.

EXAMPLES

Example 1

A sodium chlorite cell of the type described in FIG. 1 having copper electrodes was employed. A solution of 25% active sodium chlorite including 25% NaClO2, 1.1% NaOH, 0.25% Na2CO3 and 0.3% NaCl was placed in the electrolytic cell. A direct current power supply of 18 VDC at 80 mA was used and a recycling relay was set for 10 seconds on and 50 seconds off. The cell was placed in a sealed 10 gallon chamber. An air pump was installed to purge the head space in the electrolytic cell of the chlorine dioxide generated during the on cycles. Chlorine dioxide was produced at a following rate, in air over a period of several hours.

TABLE 1

| Time | Chlorine dioxide in Air (ppm) |
| --- | --- |
| 0 minutes | 0 |
| 1 minute | 0.3 |
| 2 minutes | 0.36 |
| 3 minutes | 0.40 |
| 4 minutes | 0.43 |
| 5 minutes | 0.44 |
| 6 minutes | 0.44 |
| 7 minutes | 0.45 |
| 37 minutes | 0.36 |
| 38 minutes | 0.43 |

TABLE 1-continued

| Time | Chlorine dioxide in Air (ppm) |
|---|---|
| 1 hour 55 minutes | 0.33 |
| 4 hours 20 minutes | 1.70 |
| 8 hours 10 minutes | 0.46 |

Example 2

A procedure similar to Example 1 was employed. The power source was provided by 4 D cell batteries producing 6.3 volts. The cylindrical cell of Example 1 was replaced with a glass beaker containing 100 ml of the same 25% active solution of sodium chlorite as in Example 1, above. The electrolytic cell was installed in a Manitowoc ice machine. The electrodes were formed from stainless steel. A recycling relay was used as in Example 1 and was originally set for 6 seconds on and 54 seconds off.

TABLE 2

| Date | Time | On/Off Cycling | Chlorine Dioxide in Air (ppm) |
|---|---|---|---|
| Jun. 8, 2001 | 12:00 | 6 sec/54 sec | 0 |
|  | 12:05 pm |  | 2.6 ppm |
|  | 2:00 pm |  | 1.54 ppm |
|  | 3:00 pm | 6 sec/178 sec | 0.51 ppm |
| Jun. 11, 2001 | 6:20 am |  | 3.36 ppm |
|  | 7:30 am | 6 sec/896 sec | 1.85 ppm |
|  | 9:45 am |  | 1.32 ppm |
|  | 1:40 pm |  | 0.88 ppm |
|  | 2:35 pm |  | 0.77 ppm |
| Jun. 12, 2001 | 6:30 am |  | 0.55 ppm |
|  | 10:30 am |  | 0.73 ppm |
|  | 1:15 pm |  | 0.55 ppm |
|  | 2:35 pm |  | 0.64 ppm |
|  | 4:00 pm |  | 0.10 ppm |
| Jun. 13, 2001 | 6:40 am |  | 1.52 ppm |
|  | 8:10 am |  | 0.32 ppm |
|  | 10:30 am |  | 0.80 ppm |
|  | 11:30 am |  | 0.88 ppm |
| Jun. 14, 2001 | 6:30 am |  | 0.10 ppm |
|  | 9:40 am |  | 0.36 ppm |
|  | 11:15 am |  | 0.31 ppm |
|  | 2:25 pm |  | 0.22 ppm |
| Jun. 15, 2001 | 6:45 am |  | 0.28 ppm |
|  | 9:10 am |  | 0.27 ppm |
|  | 10:20 am |  | 0.41 ppm |
|  | 1:00 pm |  | 0.48 ppm |
|  | 2:20 pm |  | 0.14 ppm |
| Jun. 18, 2001 | 6:30 am |  | 0.60 ppm |
|  | 7:30 am |  | 0.29 ppm |
|  | 9:50 am |  | 0.15 ppm |
|  | 1:20 pm |  | 0.28 ppm |
| Jun. 19, 2001 | 7:50 am |  | 0.22 ppm |
|  | 10:00 am |  | 0.25 ppm |
|  | 2:45 pm |  | 0.18 ppm |
| Jun. 20, 2001 | 6:30 am |  | 0.36 ppm |
|  | 10:45 am |  | 0.33 ppm |
|  | 2:00 pm |  | 0.19 ppm |
| Jun. 21, 2001 | 6:30 am |  | 0.06 ppm |
|  | 10:30 am |  | 0.22 ppm |
| Jun. 22, 2001 | 6:20 am |  | 0.03 ppm |
|  | 8:30 am |  | 0.47 ppm |
| Jun. 25, 2001 | 6:30 am |  | 0.04 ppm |
|  | 9:40 am |  | 0.04 ppm |
| Jun. 26, 2001 | 9:00 am |  | 0.02 ppm |
| Test terminated |  |  |  |

The recycling relay as originally set at 6 seconds on and 54 seconds off was found to produce levels of chlorine dioxide which were unnecessarily high. The recycling relay was then set for 6 second on and 178 seconds off which was still found to produce levels of chlorine dioxide in air which were unnecessarily and unacceptably high. The recycling relay was then set for 6 seconds on and 896 seconds off in order to lower the level of chlorine dioxide in the ice machine to 0.5 ppm. Changing the cyling times can be used to control the amount of chlorine dioxide in the ice machine. Having any higher level of chlorine dioxide than about 0.5 ppm in the ice machine has not been found to be beneficial.

Maintaining a level of chlorine dioxide in the range of about 0.01 to about 20 ppm, and more suitably about 0.05–0.15 ppm has been found to be sufficient for inhibiting microbial growth in ice machines.

What is claimed is:

1. A method of producing chlorine dioxide gas at the point of use for deodorizing and sanitizing the head space of an automatic ice making machine the method comprising the steps of:
   a) providing an eleotrochemical cell in said head space of said automatic ice making machine or transporting said chlorine dioxide into said head space through a tube or vent from said electrochemical cell:
   b) electrochemically generating chlorine dioxide gas in said electrochemical cell at the point-of-use; and
   c) providing the generated chlorine dioxide gas to said head space of said automatic ice making machine to maintain a level of about 0.05 to about 20 ppm of chlorine dioxide in said enclosed space.

2. A method of producing chlorine dioxide gas at the point-of-use for deodorizing and sanitizing the head space of an automatic ice making machine, the method comprising the steps of:
   a) providing an electrolytic cell in said head space of said automatic ice making machine or said electrolytic cell connected to said head space by a vent or tub the electrolytic cell having electrodes, a gas collection space and a liquid metal chlorite composition;
   b) activating said electrolytic cell with a power source;
   c) cycling the power source on for a predetermined time interval and off for a predetermine time interval;
   d) purging the gas collection space of the electrolytic cell of chlorine dioxide gas with air said air displacing said chlorine dioxide and forcing said chlorine dioxide gas into said enclosed space.

3. The method of claim 2 wherein said purging step is accomplished with an air pump.

4. The method of claim 2 wherein said metal chlorite is an alkali metal chlorite.

5. The method of claim 4 wherein said alkali metal is sodium, potassium, or mixtures thereof.

6. The method of claim 2 wherein said metal chlorite is present at a concentration of about 10% to about 50%.

7. The method of claim 2 wherein the sodium chlorite is present at a concentration of about 25%.

8. The method of claim 2 wherein said power source is about 1 volt or higher.

9. The method of claim 2 wherein said power source is on for about 1 second to 1 minute and off for about 5 second to 5 minutes.

10. The method of claim 2 wherein said power source is on for about 10 seconds and off for about 50 seconds.

11. A device for producing chlorine dioxide gas at the point-of-use, in an ice machine, the device comprising:
   a) an electrolytic cell in contact with said ice machine containing a metal chlorite solution;
   b) a power source: and
   c) an air pump for purging chlorine dioxide gas from the head space of the electrolytic cell into the head space of the ice machine.

12. The device of claim 11 wherein said metal chlorite is present at a concentration of about 10% to about 50%.

13. The device of claim 11 wherein said metal chlorite is present at a concentration of about 25%.

14. The device of claim 11 wherein said metal chlorite is an alkali metal chlorite.

15. The device of claim 14 wherein said alkali metal is sodium, potassium, or mixtures thereof.

16. The device of claim 11 further having a programable controller for cycling the power source on for a predetermined time interval and off for a predetermined time interval.

17. The device of claim 11 wherein said power source comprises at least one battery having a voltage rating of about 1 volt or higher.

18. The device of claim 11 further comprising a relay switch in communication with said electrolytic cell having an on state and an off state.

19. The device of claim 18 wherein said relay switch is constructed and arranged to cycle between the on state and the off state at predetermined time intervals.

20. The device of claim 19 said recycling relay constructed and arranged to have an on state of about 1 second to about 1 minute on and off state of about 5 seconds to about 5 minutes.

21. The device of claim 19 said recycling relay constructed and arranged to have an on state of about 10 seconds and an off state of about 50 seconds.

22. The device of claim 11 wherein the elcotrolytic cell has copper or stainless steel electrodes.

23. The device of claim 11 said ice machine having a holder for said electrolytic cell.

24. The device of claim 23 said ice machine having a top and a front, said holder on said top of in said front of said ice machine.

25. The device of claim 19 said ice machine having ahead space and said electrolytic is in said head space.

26. A method of producing chlorine dioxide gas at the point of use for deodorizing and sanitizing in a refrigerated unit designed for dispensing items for human consumption, the method comprising the steps of;

a) providing an electrochemical cell in said refrigerated unit or transporting said chlorine dioxide to said refrigerated unit through a tube or vent from said electrochemical cell;

b) electrochemically generating chlorine dioxide gas in said electrochemical cell at the point-of-use; and c) providing the generated chlorine dioxide gas to said refrigerated unit to maintain a level of about 0.05 to about 20 ppm of chlorine dioxide in said refrigerated unit.

* * * * *